United States Patent
Son et al.

(10) Patent No.: US 10,263,959 B2
(45) Date of Patent: Apr. 16, 2019

(54) METHOD FOR COMMUNICATING MEDICAL DATA

(71) Applicant: SAMSUNG ELECTRONICS CO., LTD., Suwon-si, Gyeonggi-do (KR)

(72) Inventors: Sung-Hoon Son, Suwon-si (KR); Ki-Hyoun Kwon, Hwaseong-si (KR); Seung-Ho Lee, Hwaseong-si (KR); Jun-Ho Lee, Hwaseong-si (KR); Jerome Han, Daejeon (KR)

(73) Assignee: SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 503 days.

(21) Appl. No.: 14/946,382

(22) Filed: Nov. 19, 2015

(65) Prior Publication Data
US 2016/0156599 A1    Jun. 2, 2016

Related U.S. Application Data

(60) Provisional application No. 62/085,372, filed on Nov. 28, 2014.

(30) Foreign Application Priority Data

Apr. 8, 2015    (KR) ........................ 10-2015-0049561

(51) Int. Cl.
*H04L 29/06*    (2006.01)
*G06F 19/00*    (2018.01)
(Continued)

(52) U.S. Cl.
CPC .......... *H04L 63/0428* (2013.01); *G06F 19/32* (2013.01); *G06F 21/53* (2013.01);
(Continued)

(58) Field of Classification Search
CPC . H04L 63/0428; H04L 63/6245; G06F 21/53; G06F 21/6245
See application file for complete search history.

(56) References Cited

U.S. PATENT DOCUMENTS 7,359,518 B2 *   4/2008   Brickell ............. G06F 21/6245
                                                          380/283
7,890,748 B1 *   2/2011   Wyatt ................ H04L 63/0272
                                                          713/150
(Continued)

FOREIGN PATENT DOCUMENTS

KR    1020080033654    4/2008
KR    1020100052271    5/2010
(Continued)

*Primary Examiner* — Saleh Najjar
*Assistant Examiner* — Devin E Almeida
(74) *Attorney, Agent, or Firm* — F. Chau & Associates, LLC

(57) ABSTRACT

A method for communicating medical data includes forming a secure channel between a first medical device and a second medical device connected to each other through a network on the basis of first authentication information of the first medical device and second authentication information of the second medical device; encrypting medical data that is obtained by the first medical device using a secure circuit that is provided in the first medical device; and transmitting the encrypted medical data to the second medical device through the secure channel.

18 Claims, 10 Drawing Sheets

(51) Int. Cl.
*G06F 21/53* (2013.01)
*G06F 21/62* (2013.01)

(52) U.S. Cl.
CPC ...... *G06F 21/6245* (2013.01); *H04L 63/0464* (2013.01); *G06F 2221/2105* (2013.01)

(56) References Cited

U.S. PATENT DOCUMENTS

| | | | |
|---|---|---|---|
| 8,180,060 B2 | 5/2012 | Aizu et al. | |
| 8,554,689 B2 | 10/2013 | Mardikar et al. | |
| 9,449,196 B1* | 9/2016 | Purri | G06F 17/5022 |
| 2007/0197878 A1 | 8/2007 | Shklarski | |
| 2010/0122083 A1* | 5/2010 | Gim | G06F 21/6245 |
| | | | 713/162 |
| 2011/0131640 A1* | 6/2011 | Canis Robles | G06F 21/606 |
| | | | 726/7 |
| 2011/0179284 A1 | 7/2011 | Suzuki et al. | |
| 2011/0314280 A1* | 12/2011 | Nonaka | A61B 5/0002 |
| | | | 713/168 |
| 2012/0060035 A1* | 3/2012 | Kalmady | G06F 21/6209 |
| | | | 713/176 |
| 2012/0297177 A1* | 11/2012 | Ghosh | G06F 21/53 |
| | | | 713/2 |
| 2014/0013406 A1 | 1/2014 | Tremlet | |
| 2014/0181959 A1 | 6/2014 | Li et al. | |
| 2014/0298026 A1* | 10/2014 | Isozaki | H04L 9/0825 |
| | | | 713/171 |
| 2014/0331279 A1* | 11/2014 | Aissi | G06F 21/53 |
| | | | 726/1 |

FOREIGN PATENT DOCUMENTS

| | | |
|---|---|---|
| KR | 1020140039361 | 4/2014 |
| KR | 1020140067588 | 6/2014 |
| KR | 1020140096245 | 8/2014 |
| KR | 1020140098872 | 8/2014 |
| WO | 2008033654 | 3/2008 |
| WO | 2013141491 | 9/2013 |

* cited by examiner

METHOD FOR COMMUNICATING MEDICAL DATA

CROSS-REFERENCE TO RELATED APPLICATIONS

This application claims priority to U.S. Provisional Patent Application No. 62/085,372 filed on Nov. 28, 2014 in the U.S. Patent and Trademark Office, and Korean Patent Application No. 10-2015-0049561 filed on Apr. 8, 2015 in the Korean Intellectual Property Office, the disclosures of which are incorporated by reference herein in their entireties.

TECHNICAL FIELD

The present inventive concept relates to a method for communicating medical data.

DESCRIPTION OF THE RELATED ART

Medical information including biological information may be managed as data that can be used in a computing system. Accordingly, medical information is transmitted and received between various devices which constitute a computing system or which are connected through a computing system network. Since the medical information of individuals should be protected, efforts have been made to prevent a third party from acquiring this form of medical information data.

SUMMARY

According to an exemplary embodiment of the present inventive concept, there is provided a method for communicating medical data comprising forming a secure channel between a first medical device and a second medical device connected to each other through a network on the basis of first authentication information of the first medical device and second authentication information of the second medical device, encrypting medical data that is obtained by the first medical device using a secure circuit that is provided in the first medical device, and transmitting the encrypted medical data to the second medical device through the secure channel.

A secure key that is stored in the secure circuit is used to encrypt the medical data.

The medical data is encrypted using an operating system that is executed in the first medical device.

An operation mode of the operating system includes a secure mode in which the secure circuit is accessible, and the medical data is encrypted in the secure mode.

The operating system uses a secure task for encrypting or decrypting the medical data, and the encrypting of the medical data that is obtained by the first medical device comprises: forming a secure channel between the secure task and the secure circuit; and encrypting the medical data using a secure key which is stored in the secure circuit and is received through the secure channel that is formed between the secure task and the secure circuit.

The medical data is encrypted using the secure circuit under control of a data processing circuit that is packaged with the secure circuit.

The method further comprises storing the encrypted medical data in the secure circuit that is provided in the first medical device.

The method further comprises decrypting the encrypted medical data that is transmitted from the first medical device using a secure circuit that is provided in the second medical device.

The second medical device comprises a medical database for storing the decrypted medical data.

The method further comprises: forming a secure channel between the second medical device and a third medical device that is connected to the second medical device through the network; and transmitting the encrypted medical data that the second medical device receives from the first medical device to the third medical device through the secure channel formed between the second medical device and the third medical device.

The forming of the secure channel between the first medical device and the second medical device comprises: transmitting the first authentication information of the first medical device to the second medical device; and transmitting the second authentication information of the second medical device to the first medical device.

According to an exemplary embodiment of the present inventive concept, there is provided a method for communicating medical data comprising receiving, in a first medical device, medical data in a non-secure mode of an operating system that operates in the first medical device, switching, in the first medical device, an operation mode of the operating system to a secure mode, forming, with the first medical device and a second medical device, a certificate-based secure channel between the first medical device and the second medical device, wherein the second medical device is connected to the first medical device through a network, encrypting, in the first medical device, the medical data using a secure component that is provided in the first medical device, and transmitting the encrypted medical data from the first medical device to the second medical device through the secure channel.

The forming of the certificate-based secure channel between the first medical device and the second medical device comprises: in the secure mode of the operating system, transmitting first authentication information of the first medical device to the second medical device; transmitting second authentication information of the second medical device to the first medical device; and forming a secure channel between the first medical device and the second medical device on the basis of the first authentication information and the second authentication information.

The operating system uses a secure task for encrypting or decrypting the medical data in the secure mode, and the encrypting of the medical data using the secure component that is provided in the first medical device comprises: in the secure mode of the operating system, forming a secure channel between the secure task and the secure component; and encrypting the medical data using a secure key which is stored in the secure component and is received through the secure channel that is formed between the secure task and the secure component.

The medical data is measured using a measuring circuit that is provided in the first medical device.

The method further comprises receiving the encrypted medical data using a network circuit that is provided in the first medical device in the secure mode of the operating system, wherein the transmitting of the encrypted medical data to the second medical device through the secure channel includes transmitting the encrypted medical data that is received through the network circuit of the first medical device to the second medical device through the secure channel.

The method further comprises decrypting the encrypted medical data that is received through the network circuit of the first medical device using the secure component in the secure mode of the operating system.

The method further comprises switching an operation mode of the operating system to the non-secure mode after the encrypted medical data is transmitted from the first medical device.

The method further comprises storing the encrypted medical data that is received through the network circuit of the first medical device in a storage circuit that is provided in the first medical device in the secure mode of the operating system.

According to an exemplary embodiment of the present inventive concept, there is provided a method for communicating medical data comprising transmitting first authentication information of a first medical device to a second medical device, transmitting second authentication information of the second medical device to the first medical device, forming a secure channel between the first medical device and the second medical device on the basis of the first authentication information and the second authentication information, measuring medical data using a measuring circuit that is provided in the first medical device, storing the measured medical data in a secure circuit that forms a system in package with the measuring circuit, encrypting the medical data using a secure key that is stored in the secure circuit, and transmitting the encrypted medical data to the second medical device through the secure channel.

According to an exemplary embodiment of the present inventive concept, there is provided a method for communicating medical data comprising: transmitting medical information from a first device to a second device via a first secure-channel, wherein the first secure channel is formed by performing certificate-based mutual authentication using a key with the first and second devices; encrypting the medical information at the second device; and transmitting the encrypted medical information from the second device to a third device via a second secure channel, wherein the second secure channel is formed by performing certificate-based mutual authentication using the key with the second and third devices.

The first device is a portable medical data acquisition device.

The first, second and third devices are connected to each other in a network.

BRIEF DESCRIPTION OF THE DRAWINGS

The above and other features of the present inventive concept will become more apparent by describing in detail exemplary embodiments thereof in conjunction with the accompanying drawings, in which.

DETAILED DESCRIPTION OF THE EMBODIMENTS

Figure 1:
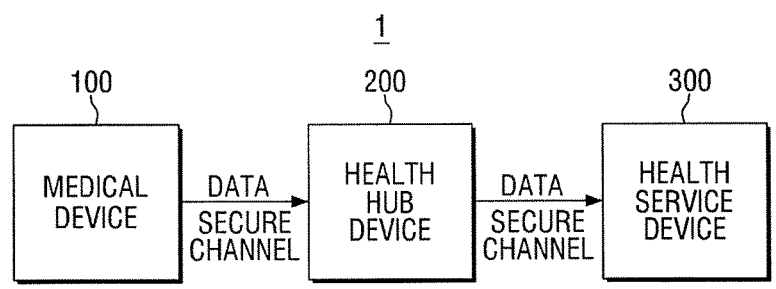
FIG. 1 is a schematic diagram of a system for communicating medical data according to an exemplary embodiment of the present inventive concept.

Hereinafter, exemplary embodiments of the present inventive concept will be described in detail with reference to the accompanying drawings.

The inventive concept, however, may be embodied in various different forms, and should not be construed as being limited only to the illustrated embodiments. Like reference numerals may denote like elements throughout the attached drawings and written description, and thus descriptions may not be repeated.

As used herein, the singular forms "a", "an" and "the" are intended to include the plural forms as well, unless the context clearly indicates otherwise.

It will be understood that when an element is referred to as being "connected to", "coupled to", or "adjacent to" another element, it can be directly connected, coupled, or adjacent to the other element, or intervening elements may be present.

FIG. 1 is a schematic diagram of a system for communicating medical data according to an exemplary embodiment of the present inventive concept.

Referring to FIG. 1, a system 1 for communicating medical data according to an exemplary embodiment of the present inventive concept may include a medical device 100, a health hub device 200, and a health service device 300.

The medical device 100 may measure medical information including biological information, and transmit the measured medical information to the health hub device 200. The medical information may include various pieces of biological information related to a human body, for example, blood pressure values, blood glucose values, oxygen saturation, heart rate, and weight. The measured medical information may be self-processed by the medical device 100, and be provided to a user, for example, through a display provided on the medical device 100. In addition, the measured medical information may be transmitted to another device that is connected to the medical device 100 through a network to be processed. In the case where the medical device 100 transmits medical information to another device, the medical device 100 may form a certificate-based secure channel, and then transmit encrypted medical data through the secure channel.

In an exemplary embodiment of the present inventive concept, the secure channel may be formed by performing certificate-based mutual authentication using a key (e.g., a public key) for the medical device 100 and the other device.

In an exemplary embodiment of the present inventive concept, the medical device 100 may be medical measurement equipment including a sphygmomanometer, a blood analysis device, and a heart rate sensor. In an exemplary embodiment of the present inventive concept, the medical device 100 may include a computing system having sensors for measurement, for example, a personal computer having measurement sensors, a server, a mobile device, or a wearable device. However, the present inventive concept is not limited thereto.

The health hub device 200 may receive the medical data from the medical device 100 through the network, and provide the medical data to the health service device 300. For example, the health hub device 200 may receive raw medical data that is directly acquired from a human body using the medical device 100, process the received medical data, and then provide the processed medical data to the health service device 300 that provides a medical service to persons on the basis of the medical data. In this case, the health hub device 200 may form the certificate-based secure channel, and then transmit the encrypted medical data to the health service device 300 through the secure channel.

In an exemplary embodiment of the present inventive concept, the health hub device 200 may include a computing system with a network function, for example, a computer, a server, a mobile device, or a wearable device. In an exemplary embodiment of the present inventive concept, the health hub device 200 may include an electronic appliance including a television receiver or a refrigerator with a network function, or include network devices including network hub equipment that performs a network function. However, the present inventive concept is not limited thereto.

The health service device 300 may decrypt the medical data that is received through the secure channel from the health hub device 200, and then be used to provide medical services to persons through processing or analysis of the medical data. Medical services may be related to keeping a patient healthy, preventing a disease, or diagnosing an illness, for example. In an exemplary embodiment of the present inventive concept, the health service device 300 may be a computing system including a server that is installed in a place where the medical service is provided, such as a hospital, but the present inventive concept is not limited thereto. For example, the server may not be located in the hospital and may be accessible via the cloud.

Hereafter, referring to FIGS. 2 to 4, the medical device 100, the health hub device 200, and the health service device 300 will be described in detail.

Figure 2:
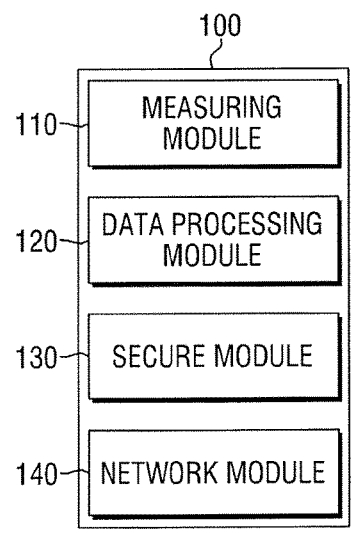
FIG. 2 is a schematic diagram of a medical device in a system for communicating medical data according to an exemplary embodiment of the present inventive concept.

FIG. 2 is a schematic diagram of a medical device in a system for communicating medical data according to an exemplary embodiment of the present inventive concept.

Referring to FIG. 2, the medical device 100 according to an exemplary embodiment of the present inventive concept may include a measuring module 110, a data processing module 120, a secure module 130, and a network module 140. Each of the modules 110, 120, 130 and 140 may constitute a circuit.

The measuring module 110 may measure medical data including biological information from a human body. In an exemplary embodiment of the present inventive concept, the measuring module 110 may include a medical sensor configured to measure the biological information from the human body and a memory module configured to store values that are measured through the medical sensor.

The data processing module 120 may receive the medical data that is measured by the measuring module 110, and form the security channel for transmitting the medical data to another device. In this case, the secure channel that is formed by the data processing module 120 may include the certificate-based secure channel, but the present inventive concept is not limited thereto.

For example, in the case where the medical device 100 transmits the medical data to another medical device, the data processing module 120 may mutually exchange authentication information of the medical device 100 and the other medical device to form the secure channel between the medical device 100 and the other medical device. The authentication information may include public information (e.g., a public key) or signature information for performing certificate-based mutual authentication. For example, the authentication information of the medical device 100 may be transmitted to the other medical device, and the authentication information of the other medical device may be transmitted to the medical device 100. Next, the data processing module 120 of the medical device 100 and the data processing module of the other medical device may form the secure channel using the received authentication information.

In an exemplary embodiment of the present inventive concept, the other medical device may be the health hub device 200. In this case, the exchanging of the authentication information and the forming of the secure channel between the medical device 100 and the health hub device 200 may be performed between the data processing module 120 of the medical device 100 and a processor 210 of the health hub device 200 to be described later.

In addition, the data processing module 120 may encrypt the medical data to safely transmit the medical data that is measured by the measuring module 110 to the secure channel. The details of the data processing module 120 and the secure module 130 will now be described.

The secure module 130 may include the secure information for encrypting the measured medical data, and store the measured medical data therein. In this case, the secure module 130 may be a hardware device which includes an electrical circuit or a chip that is electrically connected to the data processing module 120 to send and receive data to/from the data processing module 120. For example, in this case, the secure module 130 may be a secure chip which stores therein a secure key that is used to encrypt the medical data.

The data processing module 120 may encrypt the medical information that is measured by the measuring module 110 using the secure module 130 provided in the medical device 100. For example, the data processing module 120 may first draw the secure information that is stored in the secure module 130, e.g., the secure key that is stored in the secure chip, and then encrypt the medical data using the secure key.

In addition, the data processing module 120 may decrypt the encrypted medical data. In this case, the data processing module 120 may decrypt the encrypted medical data using the secure module 130 that is provided in the medical device 100. In other words, the data processing module 120 may decrypt the encrypted medical data using the secure information stored in the secure module 130, e.g., using the secure key stored in the secure chip.

In an exemplary embodiment of the present inventive concept, the measured medical data, the medical data encrypted using the secure key, or the medical data decrypted using the secure key may be stored in the secure module 130. In addition, in an exemplary embodiment of the present inventive concept, the medical device 100 may include a database for performing storage, searches, and analysis with respect to the decrypted medical data.

The network module 140 may transmit the encrypted medical data to another device through the secure channel that is formed by the data processing module 120. In an exemplary embodiment of the present inventive concept, a network in which the secure channel is formed may include a wired network including a Local Area Network (LAN) or a Wide Area Network (WAN) and a wireless network including a WiFi network, a cellular network, or a Bluetooth network, but the present inventive concept is not limited thereto.

Figure 3:
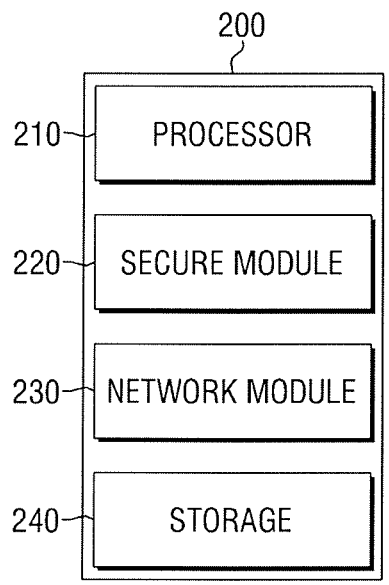
FIG. 3 is a schematic diagram of a health hub device in a system for communicating medical data according to an exemplary embodiment of the present inventive concept.

FIG. 3 is a schematic diagram of a health hub device in a system for communicating medical data according to an exemplary embodiment of the present inventive concept.

Referring to FIG. 3, the health hub device 200 according to an exemplary embodiment of the present inventive concept may include a processor 210, a secure module 220, a network module 230, and a storage 240. Each of the processor 210, the modules 220 and 230 and the storage 240 may constitute a circuit.

The processor 210 may form a secure channel for transmitting medical data that is received from the medical device 100 to the health service device 300. Further, the processor 210 may encrypt the medical data to safely transmit the medical data, or decrypt the medical data that is received from the medical device 100, e.g., the encrypted medical data.

In this case, the secure channel that is formed by the processor 210 may include a certificate-based secure channel, but the present inventive concept is not limited thereto. For example, in the case where the health hub device 200 transmits the medical data to the health service device 300, the processor 210 may mutually exchange authentication information of the health hub device 200 and the health service device 300 to form the secure channel between the health hub device 200 and the medical service device 300. For example, the authentication information of the health hub device 200 may be transmitted to the health service device 300, and the authentication information of the health service device 300 may be transmitted to the health hub device 200. Next, the processors 210 and 310 of the health hub device 200 and the health service device 300 may form the secure channel using the received authentication information.

The secure module 220 may include the secure information for encrypting the medical data, and store the medical data therein. In this case, the secure module 220 may be a hardware device which includes an electrical circuit or a chip that is electrically connected to the processor 210 of the health hub device 200 to send and receive data to/from the processor 210. For example, in this case, the secure module 220 may be a secure chip which stores therein a secure key that is used to encrypt the medical data.

The processor 210 may encrypt the medical information using the secure module 220 provided in the health hub device 200. For example, the processor 210 may first draw the secure information that is stored in the secure module 220, e.g., the secure key that is stored in the secure chip, and then encrypt the medical data using the secure key.

In addition, the processor 210 may decrypt the encrypted medical data that is received from the medical device 100. In this case, the processor 210 may decrypt the encrypted medical data using the secure module 220 that is provided in the health hub device 200. In other words, the processor 210 may decrypt the encrypted medical data that is received from the medical device 100 using the secure information stored in the secure module 220, e.g., using the secure key stored in the secure chip.

In an exemplary embodiment of the present inventive concept, the measured medical data, the medical data encrypted using the secure key, or the medical data decrypted using the secure key may be stored in the secure module 220.

The network module 230 may transmit the encrypted medical data to the health service device 300 through the secure channel that is formed by the processor 210. In an exemplary embodiment of the present inventive concept, a network in which the secure channel is formed may include a wired network including a LAN or a WAN and a wireless network including a WiFi network, a cellular network, or a Bluetooth network, but the present inventive concept is not limited thereto.

The storage 240 may store therein the encrypted medical data using the measured medical data, the medical data encrypted using the secure key, or the medical data decrypted using the secure key. In an exemplary embodiment of the present inventive concept, the storage 240 may include a Hard Disk Drive (HDD), a Solid State Drive (SSD), or a network storage, but the present inventive concept is not limited thereto.

Figure 4:
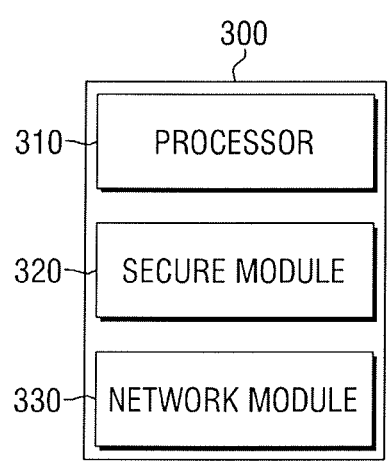
FIG. 4 is a schematic diagram of a health service device in a system for communicating medical data according to an exemplary embodiment of the present inventive concept.

FIG. 4 is a schematic diagram of a health service device in a system for communicating medical data according to an exemplary embodiment of the present inventive concept.

Referring to FIG. 4, the health service device 300 according to an exemplary embodiment of the present inventive concept may include a processor 310, a secure module 320, and a network module 330. Each of the processor 310 and the modules 320 and 330 may constitute a circuit.

The processor 310 may receive the medical data from the health hub device 200, and decrypt the medical data that is received from the health hub device 200, e.g., the encrypted medical data.

The secure module 320 may include the secure information for decrypting the medical data, and the processor 310 may decrypt the encrypted medical data that is received from the health hub device 200 using the secure information stored in the secure module 320, e.g., the secure key stored in the secure chip.

The network module 330 may receive the encrypted medical data from the health hub device 200 through the secure channel that is formed by the processor 310.

Figure 5:
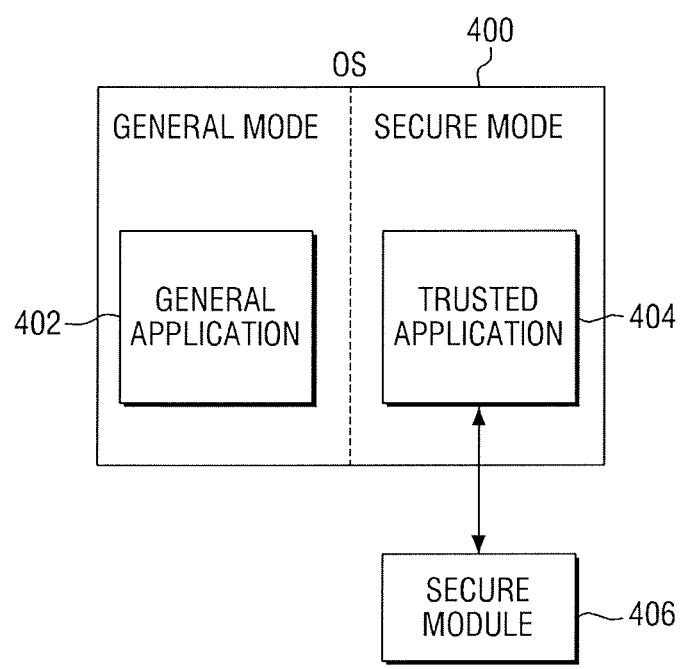
FIG. 5 is a schematic diagram of an operating system that is executed in a medical device according to an exemplary embodiment of the present inventive concept.

FIG. 5 is a schematic diagram of an operating system that is executed in a medical device according to an exemplary embodiment of the present inventive concept.

Referring to FIG. 5, the medical device 100 according to an exemplary embodiment of the present inventive concept may include an operating system 400 for operating the medical device 100 and controlling the operation of the medical device 100.

An operation mode of the operating system 400 may include a general mode and a secure mode. For example, a first mode and a second mode. The operating system 400 that operates in the general mode may be unable to access a secure module 406 used in the forming of the secure channel between the devices (e.g., 100, 200 and 300) and the encryption/decryption of the medical data. The operating system 400 that operates in the secure mode may be able to access the secure module 406. The secure module 406 may correspond to the secure module 130 of the medical device 100, the secure module 220 of the health hub device 200, or the secure module 320 of the health service device 300 as described above.

Accordingly, the operating system 400 that operates in the general mode, e.g., in a non-secure mode, may execute a general application 402 that requires a low secure level, whereas the operating system 400 that operates in the secure mode may execute a trusted application 404 that requires a high secure level. For example, the trusted application 404 may form the secure channel between the devices (e.g., 100, 200 and 300) and encrypt/decrypt the medical data using the secure module 406.

Figure 6:
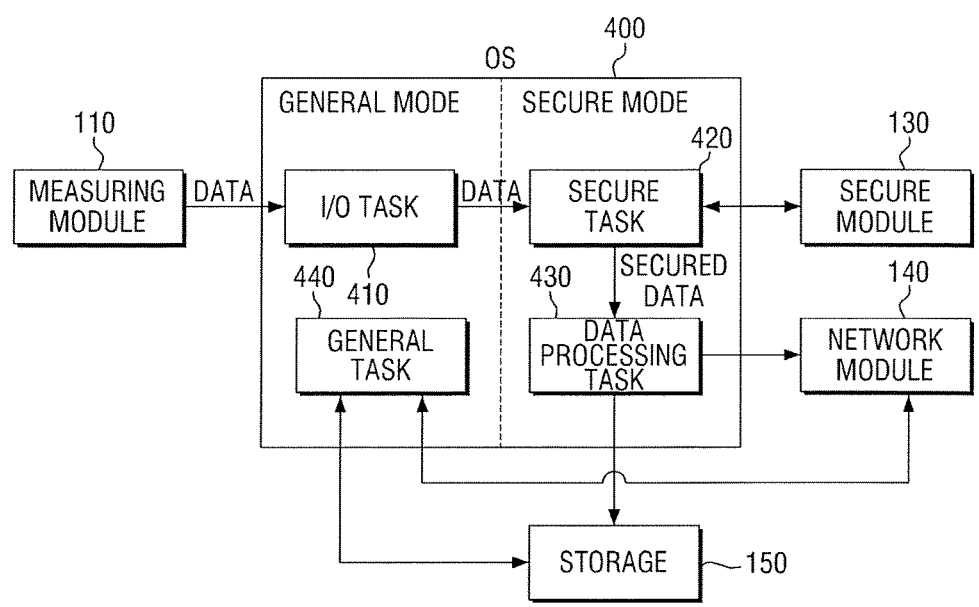
FIG. 6 is a schematic diagram of a method for communicating medical data according to an exemplary embodiment of the present inventive concept.

FIG. 6 is a schematic diagram of a method for communicating medical data according to an exemplary embodiment of the present inventive concept.

Referring to FIG. 6, an input/output (I/O) task 410 may be executed by the operating system 400 that operates in the non-secure mode. A general task 400 may also be executed by the operating system 400 that operates in the non-secure mode. The I/O task 410 may receive the measured medical data from the measuring module 110 of the medical device 100 in the non-secure mode. Next, the operation mode of the operating system 400 is switched to the secure mode.

In the secure mode, a secure task 420 for forming the secure channel between the devices (e.g., 100, 200 and 300) and encrypting/decrypting the medical data and a data processing task 430 for performing various tasks that include transmitting the encrypted medical data through a network or storing the encrypted medical data in storage 150 may be executed.

The secure task 420 may mutually exchange authentication information of the medical device 100 and another medical device 102 to form the secure channel between the medical device 100 and the other medical device. For example, the authentication information of the medical device 100 may be transmitted to the other medical device, and the authentication information of the other medical device may be transmitted to the medical device 100. Next, the respective secure tasks 420 of the medical device 100 and the other medical device may form the secure channel using the received authentication information.

In addition, the secure task 420 may encrypt the medical data using the secure module 130 that is provided in the medical device 100 to safely transmit the medical data to the secure channel. For example, the secure task 420 may first draw the secure information that is stored in the secure module 130, e.g., the secure key that is stored in the secure chip, and then encrypt the medical data using the secure key. Further, the secure task 420 may decrypt the medical data using the secure module 130 that is provided in the medical device 100.

The data processing task 430 may transmit the encrypted medical data to the other medical device through the secure channel that is formed by the secure task 420 using the network module 140 of the medical device 100.

As described above, by making the secure task 420 and the data processing task 430 operate in the secure mode, a third party's access to the medical data can be prevented.

Figure 7:
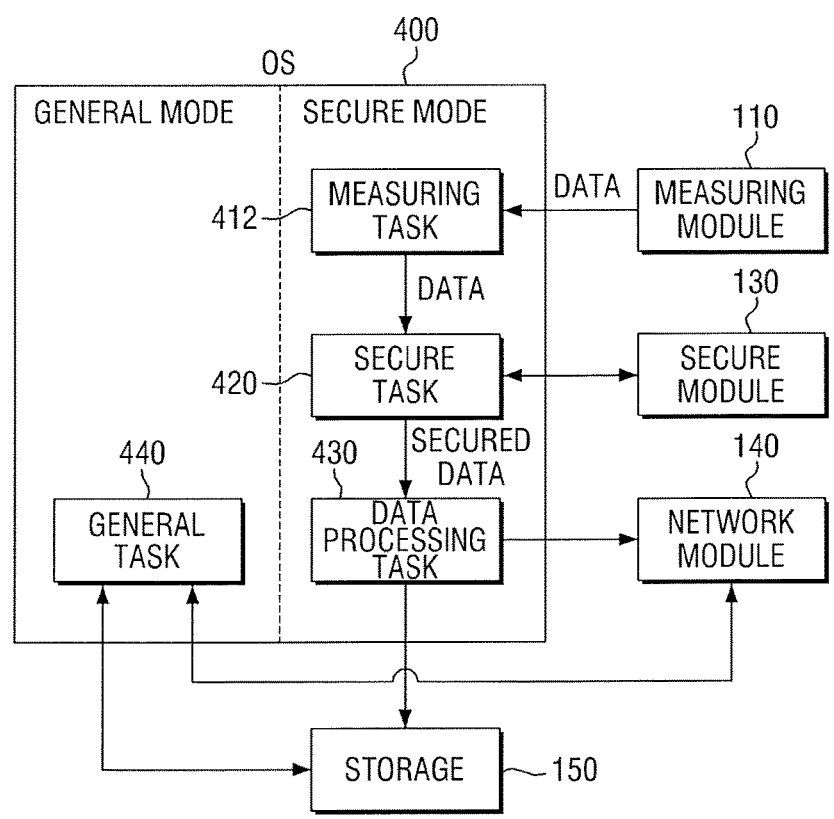
FIG. 7 is a schematic diagram of a method for communicating medical data according to an exemplary embodiment of the present inventive concept.

FIG. 7 is a schematic diagram of a method for communicating medical data according to an exemplary embodiment of the present inventive concept.

The method shown in FIG. 7 differs from the method shown in FIG. 6 in that a measuring task 412 is executed by the operating system 400 that operates in the secure mode.

The measuring task 412 may measure the medical data including biological information from the human body using the measuring module 110 of the medical device 100. Further, the measuring task 412 may transfer the measured medical data to the secure task 420. As described above, since the task for measuring the medical data may be executed in the secure mode, the amount and/or type of medical data not accessible by a third party hacker can be increased.

Figure 8:
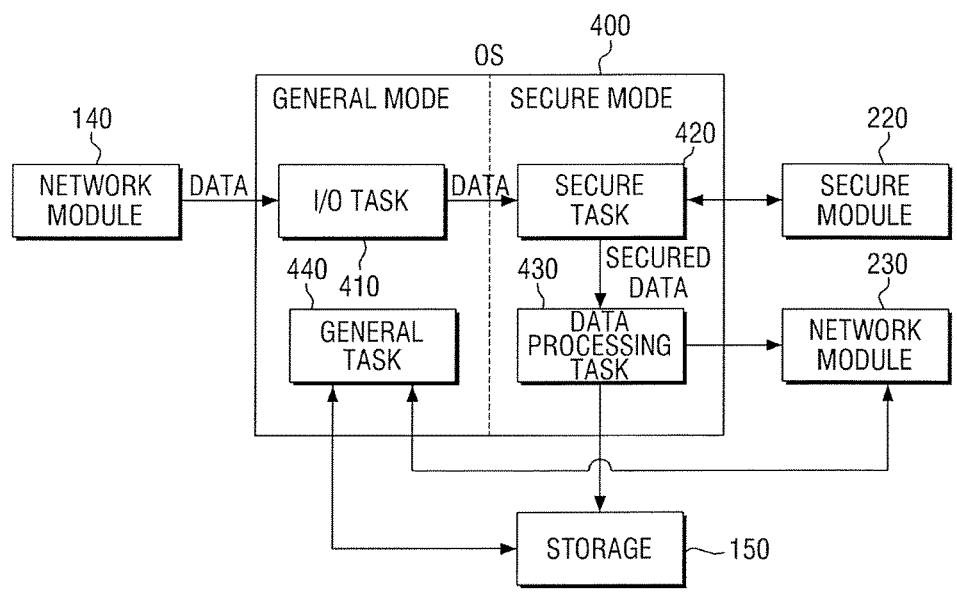
FIG. 8 is a schematic diagram of a method for communicating medical data according to an exemplary embodiment of the present inventive concept.

FIG. 8 is a schematic diagram of a method for communicating medical data according to an exemplary embodiment of the present inventive concept.

Referring to FIG. 8, the I/O task 410 may be executed by the operating system 400 that operates in the non-secure mode. The I/O task 410 may receive the measured medical data from the network module 140 of the medical device 100 in the non-secure mode. Next, the operation mode of the operating system 400 is switched to the secure mode.

The operating system 400 may be executed by another medical device that receives the medical data from the medical device 100 or the health hub device 200 that receives the medical data from the medical device 100. Since the operation of the other medical device may be the same as the medical device 100 described above, the following description will focus on the operating system 400 being executed by the health hub device 200.

In the secure mode, the secure task 420 for forming the secure channel between the devices (e.g., 100, 200 and 300) and encrypting/decrypting the medical data and the data processing task 430 for performing various tasks that include transmitting the encrypted medical data through the network or storing the encrypted medical data in the storage 150 may be executed.

The secure task 420 may mutually exchange authentication information of the health hub device 200 and the health service device 300 form the secure channel between the health hub device 200 and the health service device 300. For example, the authentication information of the health hub device 200 may be transmitted to the health service device 300, and the authentication information of the health service device 300 may be transmitted to the health hub device 200. Next, the respective secure tasks 420 of the health hub device 200 and the health service device 300 may form the secure channel using the received authentication information.

In addition, the secure task 420 may encrypt the medical data using the secure module 220 that is provided in the health hub device 200 to safely transmit the medical data to the secure channel. For example, the secure task 420 may first draw the secure information that is stored in the secure module 220, e.g., the secure key that is stored in the secure chip, and then encrypt the medical data using the secure key. Further, the secure task 420 may decrypt the medical data using the secure module 220 that is provided in the health hub device 200.

The data processing task 430 may transmit the encrypted medical data to the health service device 300 through the secure channel that is formed by the secure task 420 using the network module 230 of the health hub device 200.

As described above, by making the secure task 420 and the data processing task 430 operate in the secure mode, a third party's access to the medical data transferred between the health hub device 200 and the health service device 300 can be prevented.

Figure 9:
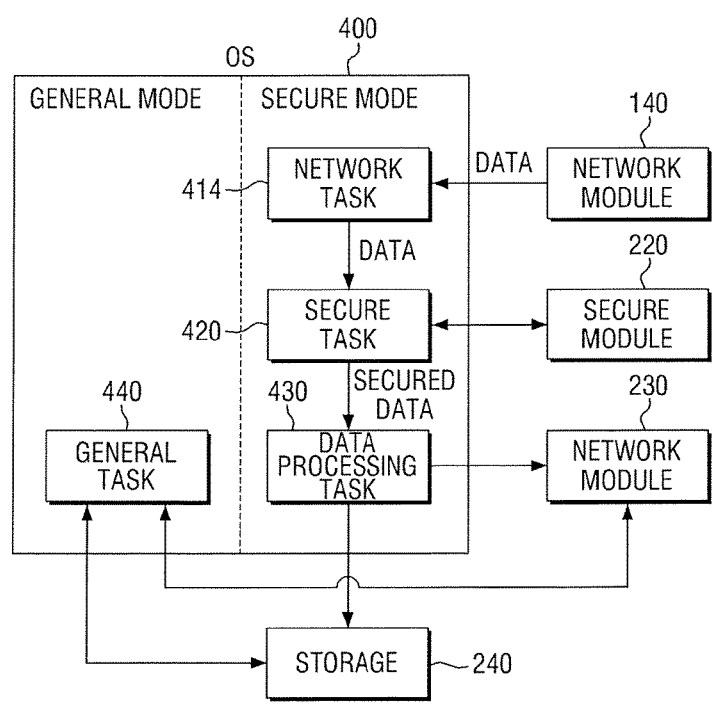
FIG. 9 is a schematic diagram of a method for communicating medical data according to an exemplary embodiment of the present inventive concept.

FIG. 9 is a schematic diagram of a method for communicating medical data according to an exemplary embodiment of the present inventive concept.

The method shown in FIG. 9 differs from the method shown in FIG. 8 in that a network task 414 is executed by the operating system 400 that operates in the secure mode. The network task 414 may receive the medical data from the network module 140 of the medical device 100, and transfer the received medical data to the secure task 420. As described above, since the network task may be executed in the secure mode, the third party's access to the medical data can be further prevented.

In the embodiments described above with reference to FIGS. 6 to 9, it is described and illustrated that the network modules 140 and 230 and the storages 150 and 240 are operated by the data processing task 430 in the secure mode, but the present inventive concept is not limited thereto. For example, in an exemplary embodiment of the present inventive concept, independent of the execution of the above-described tasks 420 (secure) and 430 (data processing) performed in the secure mode, the general task 440 may be executed in the general mode. In this case, the network modules 140 and 230 and the storages 150 and 240 may be accessed by the task that is executed in the secure mode, for example, by the data processing task 430, or be accessed by a task that is executed in the general (non-secure) mode, for example, by the general task 440.

For example, the network modules 140 and 230 may transmit data to another device through the data processing task 430 that is executed in the secure mode, or transmit the data to the other device through the general task 440 that is executed in the non-secure mode. For example, in the case of transmitting the data to the other device through the general task 440, although the general task 440 is performed in the non-secure mode, the general task 400 may form a secure channel for sending and receiving the data to/from the other device, and transmit the data to the other device through the secure channel. Further, the data may include, for example, the encrypted medical data that is received from the secure task 420.

As another example, the storages 150 and 240 may store therein the data through the data processing task 430 that is executed in the secure mode, or store therein the data through the general task 440 that is executed in the non-secure mode. In this case, the data may include, for example, the encrypted medical data that is received from the secure task 420.

Figure 10:
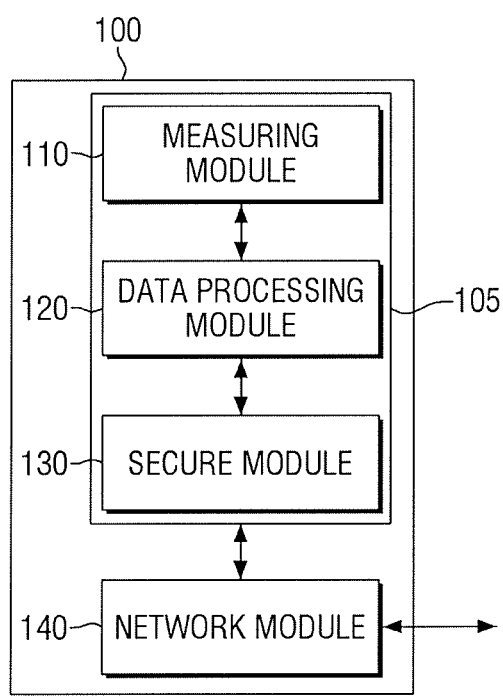
FIG. 10 is a schematic diagram of a medical device according to an exemplary embodiment of the present inventive concept.

FIG. 10 is a schematic diagram of a medical device according to an exemplary embodiment of the present inventive concept.

Referring to FIG. 10, the medical device 100 according to this embodiment differs from the medical device 100 as illustrated in FIG. 2 in that the measuring module 110, the data processing module 120, and the secure module 130 are included in one system in package 105.

In other words, since the measuring module 110, the data processing module 120, and the secure module 130 are physically packaged in a single package 105, a third party's access to the medical data that is measured by the measuring module 110 or the medical data that is encrypted by the data processing module 120 can be prevented. For example, there may be no wireless transmission between the measuring module 110 and the data processing module 120. Accordingly, the medical device 100 according to this embodiment may encrypt the medical data or safely transmit the medical data to another device using the packaged data processing module 120 and secure module 130 without having to employ an operating system that operates in a secure mode.

Figure 11:
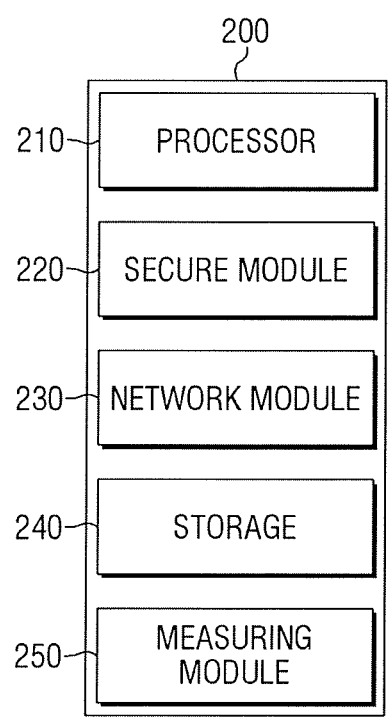
FIG. 11 is a schematic diagram of a health hub device according to an exemplary embodiment of the present inventive concept.

FIG. 11 is a schematic diagram of a health hub device according to an exemplary embodiment of the present inventive concept.

Referring to FIG. 11, the health hub device 200 according to this embodiment differs from the health hub device 200 as illustrated in FIG. 3 in that a measuring module 250 is further included in addition to the processor 210, the secure module 220, the network module 230, and the storage 240. Accordingly, the health hub device 200 according to this embodiment may transmit the medical data that is received from the medical device 100 to the health service device 300, or transmit the medical data that is directly measured by the health hub device 200 to the health service device 300.

Figure 12:
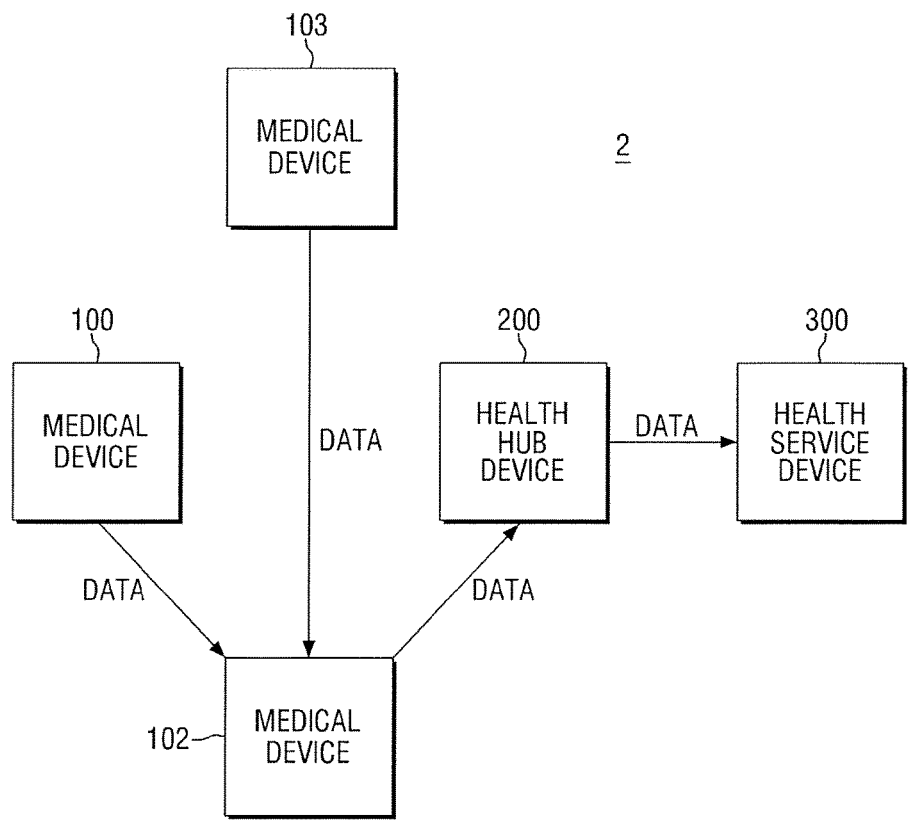
FIG. 12 is a schematic diagram of a system for communicating medical data according to an exemplary embodiment of the present inventive concept.

FIG. 12 is a schematic diagram of a system for communicating medical data according to an exemplary embodiment of the present inventive concept.

Referring to FIG. 12, a system 2 for communicating medical data according to this embodiment includes medical devices 100, 102, and 103, a health hub device 200, and a health service device 300.

The system 2 for communicating medical data according to this embodiment differs from the system 1 for communicating medical data as illustrated in FIG. 1 in that the medical data is transmitted between medical devices 100, 102, and 103. For example, the system 2 may form a secure channel between the medical device 100 and the medical device 102, and transmit the medical data that is measured by the medical device 100 to the medical device 102 through the secure channel that is formed between the medical device 100 and the medical device 102. Next, the system 2 may form a secure channel between the medical device 102 and the health hub device 200, and transmit the medical data that is measured by the medical device 102 to the health hub device 200 through the secure channel that is formed between the medical device 102 and the health hub device 200.

Further, the system 2 may form a secure channel between the medical device 103 and the medical device 102, and transmit the medical data that is measured by the medical device 103 to the medical device 102 through the secure channel that is formed between the medical device 103 and the medical device 102. In this case, the medical device 102 may transmit all the medical data received from the medical devices 100 and 103 to the health hub device 200. Although FIG. 12 shows the medical device 102 receiving and transmitting the medical data from the medical devices 100 and 103 to the health hub device 200, the present inventive concept is not limited thereto. For example, the medical device 103 can be used to receive and transmit the medical data from the medical devices 100 and 102 to the health hub device 200.

In the manner described above, the secure channel between the medical devices 100 and 102 may be formed on the basis of the certificate of the medical device 100 and the certificate of the medical device 102, and the secure channel between the medical devices 103 and 102 may be formed on the basis of the certificate of the medical device 103 and the certificate of the medical device 102. Further, the secure channel between the medical device 102 and the health hub device 200 may be formed on the basis of the certificate of the medical device 102 and the certificate of the health hub device 200.

Figure 13:
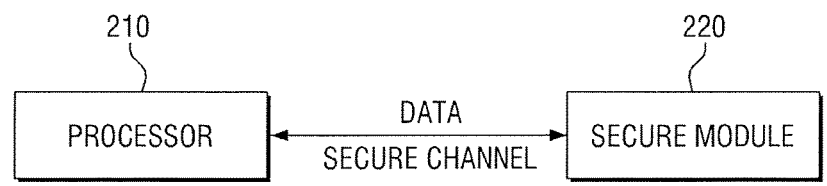
FIG. 13 is a schematic diagram of a method for communicating medical data according to an exemplary embodiment of the present inventive concept.

FIG. 13 is a schematic diagram of a method for communicating medical data according to an exemplary embodiment of the present inventive concept.

Referring to FIG. 13, the operating system 400 of the medical device 100 or the health hub device 200 may form the secure channel along with the secure module 406 (see FIG. 5) for encrypting or decrypting the medical data in the secure mode, and receive the secure key through the secure channel.

Further, in an exemplary embodiment of the present inventive concept, the data processing module 120 of the medical device 100 may form the secure channel along with the secure module 130 of the medical device 100 for encrypting or decrypting the medical data, and receive the secure key through the secure channel. In addition, in an exemplary embodiment of the present inventive concept, the processor 210 of the health hub device 200 may form the secure channel along with the secure module 220 of the health hub device 200 for encrypting or decrypting the medical data, and receive the secure key through the secure channel.

In an exemplary embodiment of the present inventive concept, the secure channel may include the certificate-based secure channel as described above.

While the present inventive concept has been shown and described with reference to exemplary embodiments thereof, it will be understood by those skilled in the art that various modifications, additions and substitutions are possible, without departing from the scope of the inventive concept as defined by the accompanying claims.

What is claimed is:

1. A method for communicating medical data, comprising:
forming a first secure channel between a first medical device and a second medical device connected to each other through a network on the basis of first authentication information of the first medical device and second authentication information of the second medical device,
wherein the first medical device includes a measuring circuit, a data processing circuit, a secure circuit and a network circuit, the measuring circuit measuring medical data including biological information from a human body, the data processing circuit receiving the medical data that is measured by the measuring circuit and forming a second secure channel between the data processing circuit and the secure circuit, the secure circuit including secure information used for data encryption and providing the secure information to the data processing circuit via the second secure channel;
encrypting medical data that is obtained by the first medical device using the secure circuit; and
transmitting the encrypted medical data to the second medical device through the first secure channel by using the network circuit,
wherein the medical data is encrypted using an operating system that is executed in the first medical device,
wherein an operation mode of the operating system includes a secure mode in which the secure circuit is accessible, and the medical data is encrypted in the secure mode,
wherein the operating system uses a secure task for encrypting or decrypting the medical data and a data processing task for transmitting the encrypted medical data through the network circuit and storing the encrypted medical data in a storage,
wherein both the secure task and the data processing task operate in the secure mode,
wherein the secure task encrypts or decrypts the medical data only when the second secure channel between the data processing and the secure circuit is established.

2. The method of claim 1, wherein a secure key that is stored in the secure circuit is used to encrypt the medical data, wherein the secure key is part of the secure information.

3. The method of claim 1, wherein the encrypting of the medical data that is obtained by the first medical device comprises:
forming a secure channel between the secure task and the secure circuit, wherein the secure channel between the secure task and the secure circuit is the second secure channel; and
encrypting the medical data using a secure key which is stored in the secure circuit and is received through the secure channel that is formed between the secure task and the secure circuit, wherein the secure key is part of the secure information.

4. The method of claim 1, wherein the medical data is encrypted using the secure circuit under control of the data processing circuit that is packaged with the secure circuit.

5. The method of claim 1, further comprising storing the encrypted medical data in the secure circuit that is provided in the first medical device.

6. The method of claim 1, further comprising decrypting the encrypted medical data that is transmitted from the first medical device using a secure circuit that is provided in the second medical device.

7. The method of claim 6, wherein the second medical device comprises a medical database for storing the decrypted medical data.

8. The method of claim 1, further comprising:
forming a third secure channel between the second medical device and a third medical device that is connected to the second medical device through the network; and
transmitting, the encrypted medical data that the second medical device receives from the first medical device to the third medical device through the third secure channel formed between the second medical device and the third medical device.

9. The method of claim 1, wherein the forming of the first secure channel between the first medical device and the second medical device comprises:
transmitting the first authentication information of the first medical device to the second medical device; and
transmitting the second authentication information of the second medical device to the first medical device.

10. A method for communicating medical data, comprising:
receiving, in a first medical device, medical data in a non-secure mode of an operating system that operates in the first medical device;
switching, in the first medical device, an operation mode of the operating system to a secure mode;
forming, with the first medical device and a second medical device, a first certificate-based secure channel between the first medical device and the second medical device, wherein the second medical device is connected to the first medical device through a network;
forming, with the first medical device, a second certificate-based secure channel between a secure component and a data processing component that are provided in the first medical device;
encrypting, in the first medical device, the medical data provided via the second certificate-based secure channel using the secure component that is provided in the first medical device only when the second certificatedbased secure channel between the data processing component and the secure component is established; and transmitting the encrypted medical data from the first medical device to the second medical device through the first certificate-based secure channel, wherein the operating system uses a secure task for encrypting or decrypting the medical data in the secure mode, and a data processing task for transmitting the encrypted medical data through a network circuit and storing the encrypted medical data in a storage circuit in the secure mode.

11. The method of claim 10, wherein the forming of the first certificate-based secure channel between the first medical device and the second medical device comprises:

in the secure mode of the operating system, transmitting first authentication information of the first medical device to the second medical device;

transmitting second authentication information of the second medical device to the first medical device; and forming a secure channel between the first medical device and the second medical device on the basis of the first authentication information and the second authentication information.

12. The method of claim 10, wherein the encrypting of the medical data using the secure component that is provided in the first medical device comprises:

in the secure mode of the operating system, forming a secure channel between the secure task and the secure component, wherein the secure channel between the secure task and the secure component is the second certificate-based secure channel; and encrypting the medical data using a secure key which is stored in the secure component and is received through the second certificate-based secure channel that is formed between the secure task and the secure component.

13. The method of claim 10, wherein the medical data is measured using a measuring circuit that is provided in the first medical device.

14. The method of claim 10, further comprising receiving the encrypted medical data using the network circuit that is provided in the first medical device in the secure mode of the operating system, wherein the transmitting of the encrypted medical data to the second medical device through the first certificate-based secure channel includes transmitting the encrypted medical data that is received through the network circuit of the first medical device to the second medical device through the first certificate-based secure channel.

15. The method of claim 14, further comprising decrypting the encrypted medical data that is received through the network circuit of the first medical device using the secure component in the secure mode of the operating system.

16. The method of claim 15, further comprising switching an operation mode of the operating system to the non-secure mode after the encrypted medical data is transmitted from the first medical device.

17. The method of claim 14, further comprising storing the encrypted medical data that is received through the network circuit of the first medical device in the storage circuit that is provided in the first medical device in the secure mode of the operating system.

18. A method for communicating medical data, comprising:

transmitting first authentication information of a first medical device to a second medical device;

transmitting second authentication information of the second medical device to the first medical device;

forming a first secure channel between the first medical device and the second medical device on the basis of the first authentication information and the second authentication information;

measuring medical data using a measuring circuit that is provided in the first medical device;

forming a second secure channel between a data processing circuit and a secure circuit provided in the first medical device;

storing the measured medical data in the secure circuit that forms a system in package with the measuring circuit, wherein the measured medical data is provided to the secure circuit from the data processing circuit via the second secure channel;

encrypting the medical data using a secure key that is stored in the secure circuit only when the secure channel between the data processing circuit and the secure circuit is established; and transmitting the encrypted medical data to the second medical device through the first secure channel, wherein the medical data is encrypted using an operating system that is executed in the first medical device, wherein an operation mode of the operating system includes a secure mode in which the secure circuit is accessible, and the medical data is encrypted in the secure mode, wherein the operating system uses a secure task for encrypting or decrypting the medical data and a data processing task for transmitting the encrypted medical data through a network circuit and storing the encrypted medical data in a storage, wherein both the secure task and the data processing task operate in the secure mode.

* * * * *